(12) United States Patent
Smith

(10) Patent No.: US 10,736,481 B2
(45) Date of Patent: Aug. 11, 2020

(54) FLUSHABLE WIPES

(71) Applicant: Welland Medical Limited, Crawley (GB)

(72) Inventor: Rory Smith, Crawley (GB)

(73) Assignee: Welland Medical Limited, Crawley (GB)

( * ) Notice: Subject to any disclaimer, the term of this patent is extended or adjusted under 35 U.S.C. 154(b) by 0 days.

(21) Appl. No.: 14/784,895

(22) PCT Filed: Apr. 15, 2014

(86) PCT No.: PCT/EP2014/057673
§ 371 (c)(1),
(2) Date: Oct. 15, 2015

(87) PCT Pub. No.: WO2014/170348
PCT Pub. Date: Oct. 23, 2014

(65) Prior Publication Data
US 2016/0051115 A1    Feb. 25, 2016

(30) Foreign Application Priority Data

Apr. 15, 2013  (GB) .................................. 1306833.3

(51) Int. Cl.
| | | |
|---|---|---|
| *A61K 8/00* | (2006.01) | |
| *A47L 13/17* | (2006.01) | |
| *A61Q 1/14* | (2006.01) | |
| *A61K 8/58* | (2006.01) | |
| *A61K 8/73* | (2006.01) | |

(Continued)

(52) U.S. Cl.
CPC .............. *A47L 13/17* (2013.01); *A47K 10/32* (2013.01); *A61K 8/0208* (2013.01); *A61K 8/585* (2013.01); *A61K 8/731* (2013.01); *A61K 8/8135* (2013.01); *A61K 8/891* (2013.01); *A61K 8/922* (2013.01); *A61Q 1/14* (2013.01); *A61Q 17/005* (2013.01); *A61Q 19/10* (2013.01); *D04H 1/425* (2013.01); *D04H 1/4291* (2013.01);

(Continued)

(58) Field of Classification Search
CPC ...... A47L 13/17; A61K 8/0208; D04H 1/067; D04H 1/26; D04H 13/001
USPC ........ 15/209.1; 442/153, 165; 428/326, 532, 428/536
See application file for complete search history.

(56) References Cited

U.S. PATENT DOCUMENTS

| | | | | |
|---|---|---|---|---|
| 5,264,269 A | * | 11/1993 | Kakiuchi .............. | C11D 3/2003 15/104.93 |
| 5,534,589 A | * | 7/1996 | Hager .................... | B29C 67/24 525/57 |

(Continued)

OTHER PUBLICATIONS

"Guidance Document for Assessing the Flushability of Nonwoven Consume Products," Worldwide Strategic Partners, 2nd Ed. 1-225 (2009).

(Continued)

*Primary Examiner* — Matthew D Matzek
(74) *Attorney, Agent, or Firm* — Foley Hoag LLP

(57) ABSTRACT

A wipe comprises fibres selected from at least one of cellulosic material, polyvinyl acetate (PVA) or a combination thereof; together with a binder which is soluble in water at standard ambient temperature and pressure (SATP). The wipe can be flushed away and is suitable for carrying a solution. The wipe is especially suitable for carrying a solution for medical purposes.

11 Claims, 8 Drawing Sheets

(51) Int. Cl.
*A61Q 17/00* (2006.01)
*A61K 8/81* (2006.01)
*A61Q 19/10* (2006.01)
*D04H 1/425* (2012.01)
*D04H 1/587* (2012.01)
*D04H 1/4291* (2012.01)
*A61K 8/02* (2006.01)
*A61K 8/92* (2006.01)
*A61K 8/891* (2006.01)
*A47K 10/32* (2006.01)
*D04H 1/4309* (2012.01)

(52) U.S. Cl.
CPC ........... *D04H 1/4309* (2013.01); *D04H 1/587* (2013.01); *A47K 2010/3266* (2013.01)

(56) References Cited

U.S. PATENT DOCUMENTS

2008/0076314 A1* 3/2008 Blanz .................... A01N 25/34
442/327
2012/0144611 A1* 6/2012 Baker .................... A47L 13/16
15/104.93

OTHER PUBLICATIONS

"Test Protocol to Determine the Flushability of Disposable Products," UKWIR Project WM07G202 (2012).

* cited by examiner

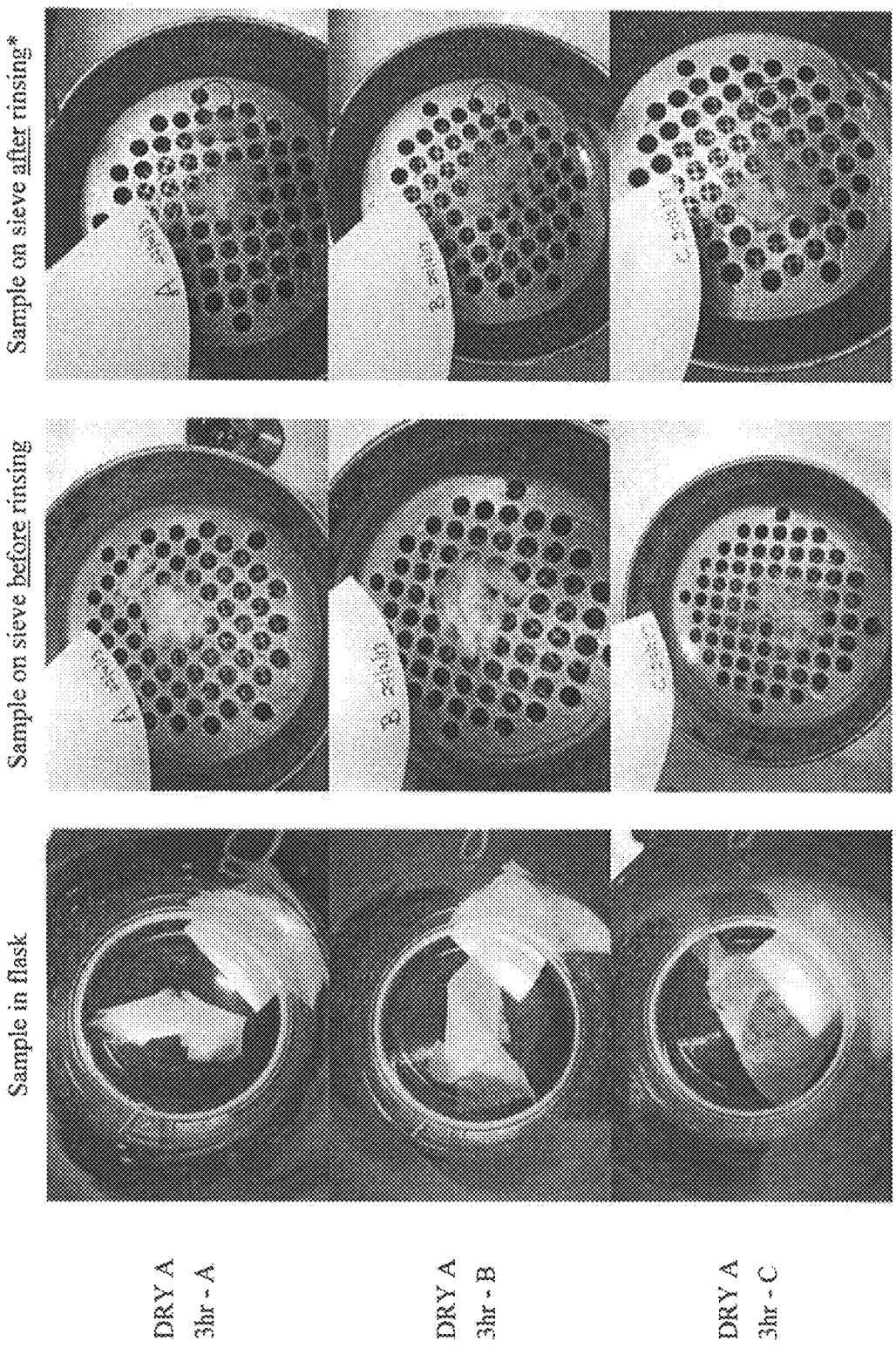
Figure 1    Product 'Dry A' – Observations for 3 hour drainline disintegration test
Note: * The circles superimposed on the images are used to assess whether the largest dimension of the remaining material is above 2.5 mm

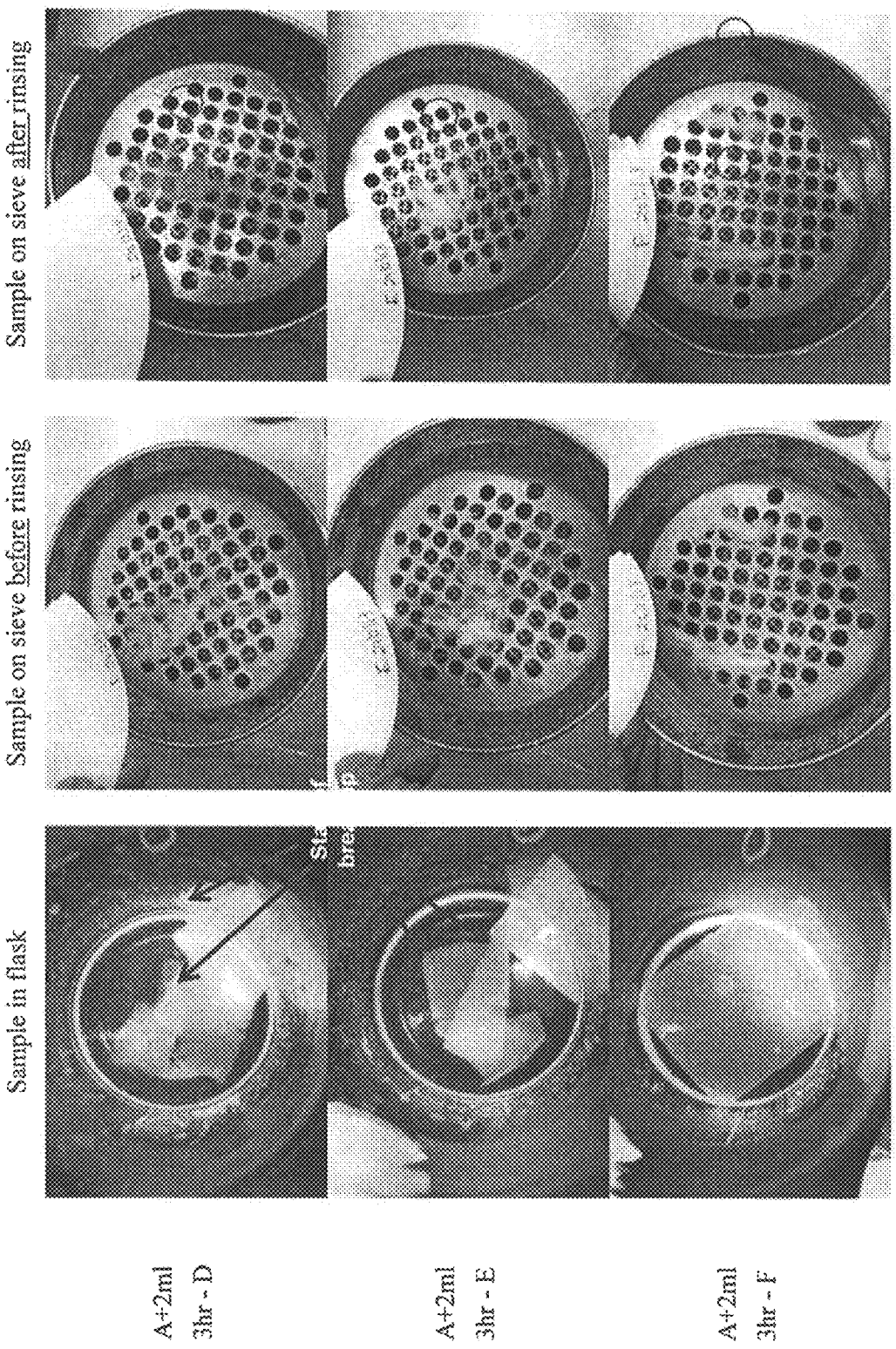
Figure 2  Product 'A + 2 ml' – Observations for 3 hour drainline disintegration test
Note: * The circles superimposed on the images are used to assess whether the largest dimension of the remaining material is above 2.5 mm

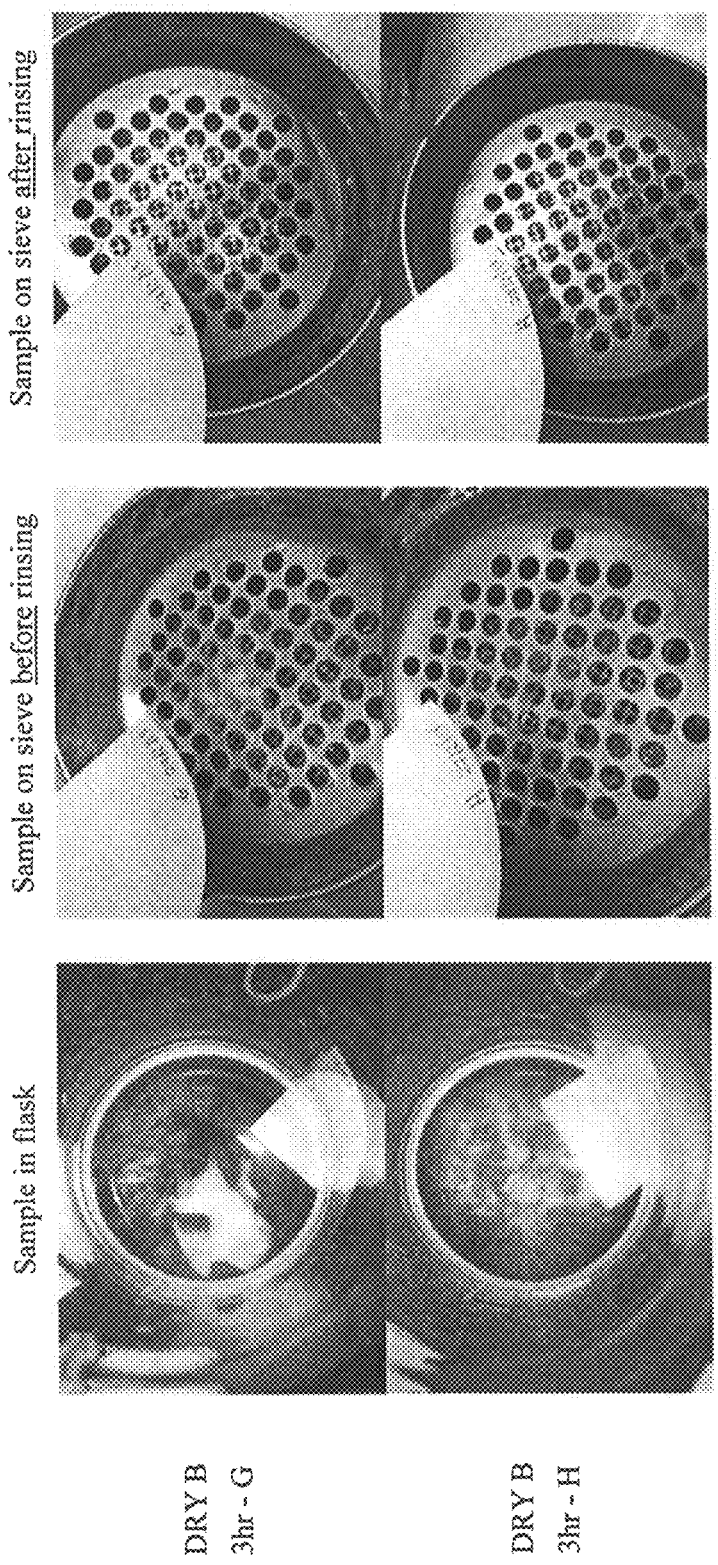
Figure 3 3 hour drainline disintegration test: observations for product 'Dry B'

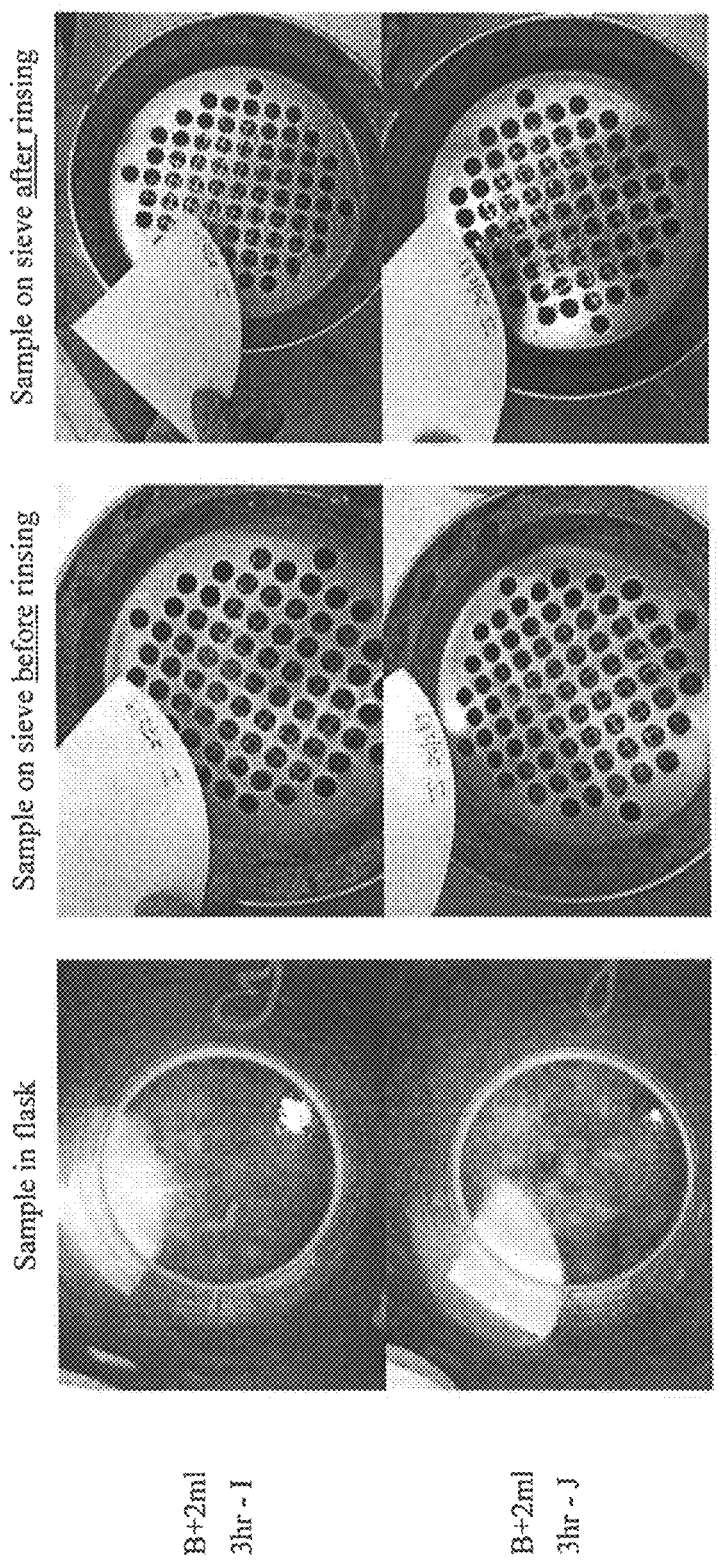
Figure 4  3 hour drainline disintegration test: observations for product 'B + 2ml'

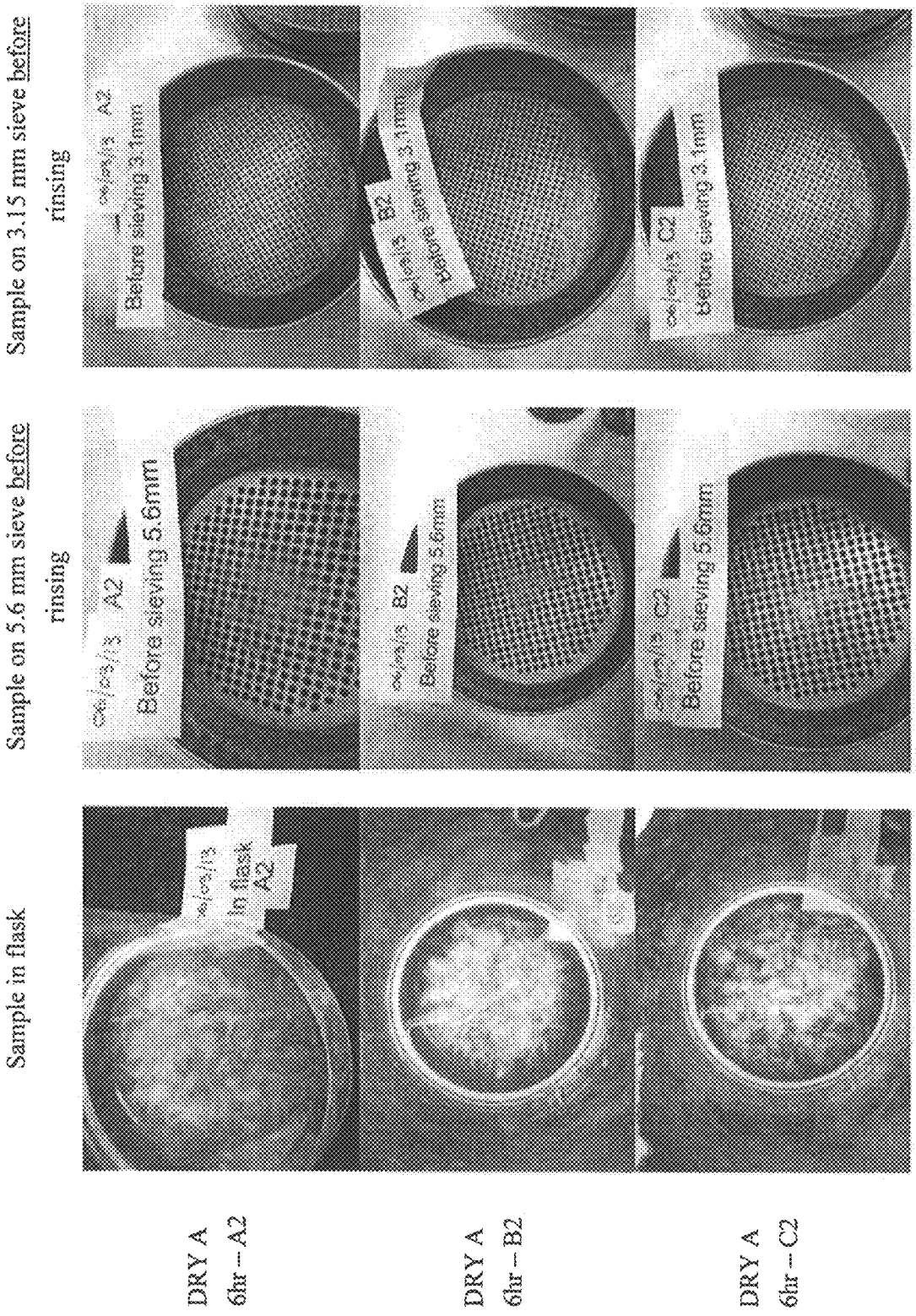
Figure 5  6 hour sewer disintegration test: observations for product 'Dry A'

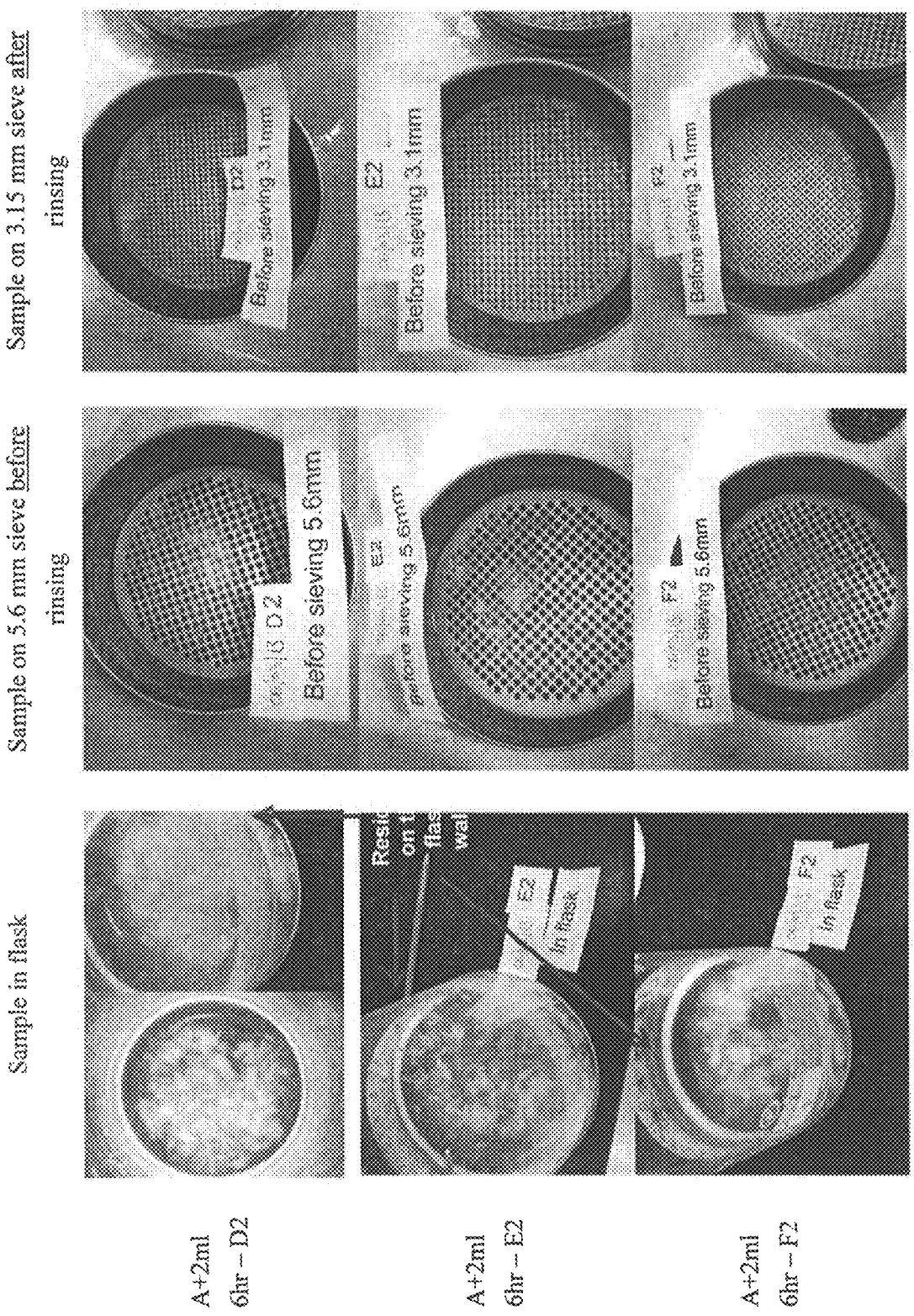
Figure 6   6 hour sewer disintegration test: observations for product 'A + 2ml'

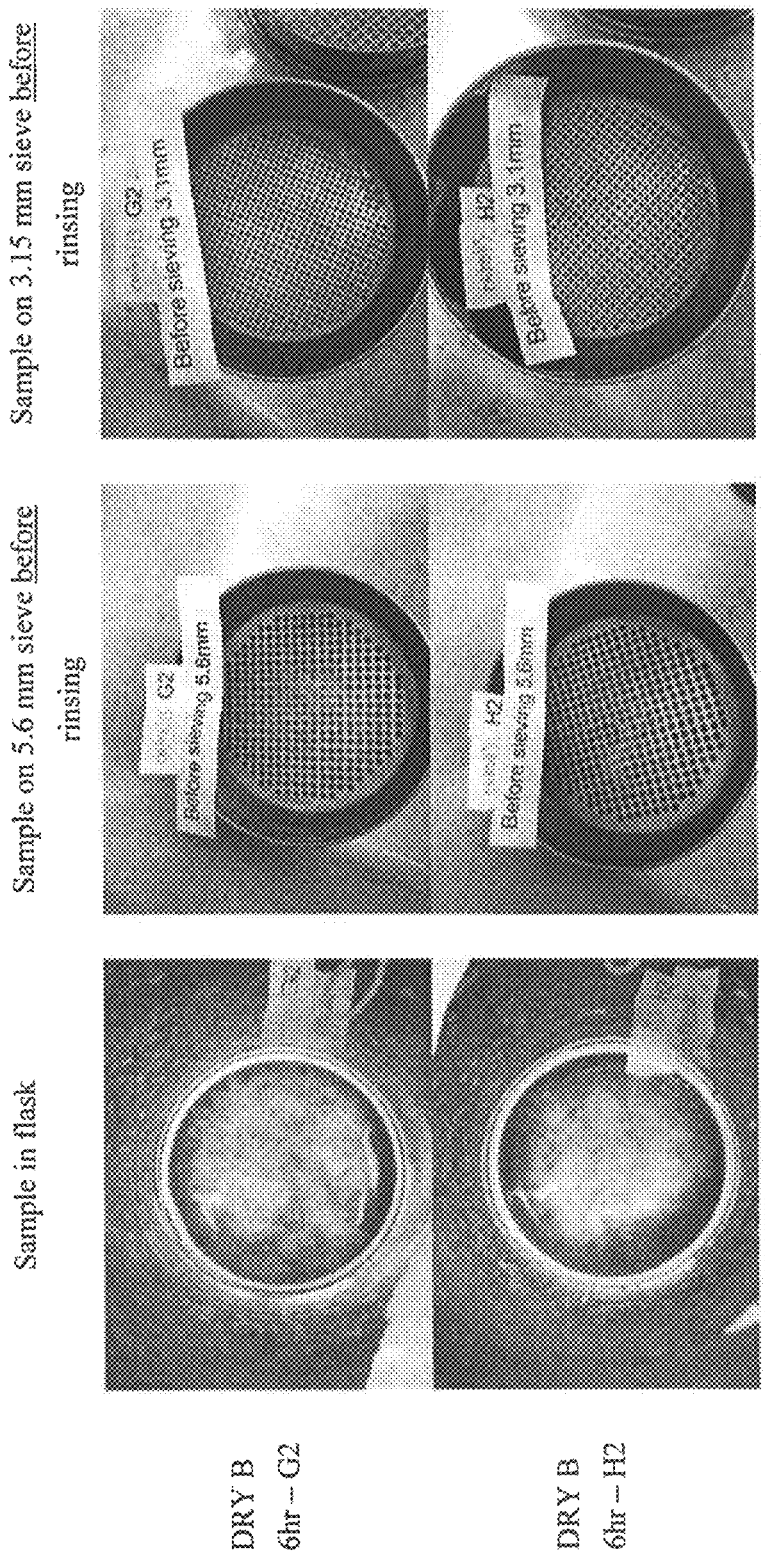
Figure 7  6 hour sewer disintegration test: observations for product 'Dry B'

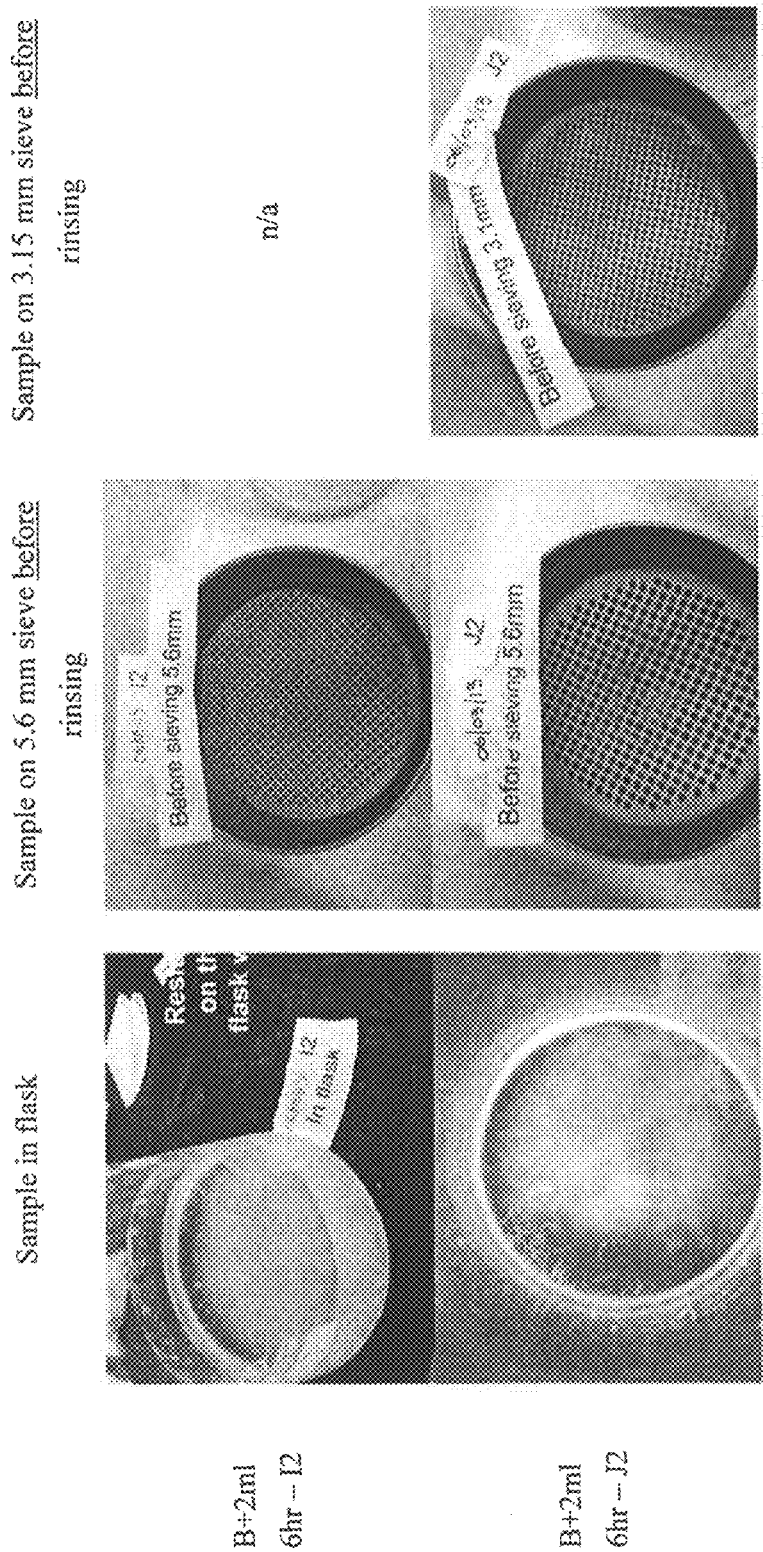
Figure 8    6 hour sewer disintegration test: observations for product 'B + 2ml'

FLUSHABLE WIPES

CROSS-REFERENCE TO RELATED APPLICATIONS

This application is the U.S. National Stage of PCT/EP2014/057673, filed Apr. 15, 2014, which claims the benefit of and priority to British Patent Application No. GB1306833.3, filed Apr. 15, 2013, both of which are hereby incorporated herein by reference in their entirety.

The present invention relates to a wipe, which can be flushed away and is suitable for carrying a solution. The wipe according to the present invention is especially suitable for carrying a solution for medical purposes.

BACKGROUND OF THE INVENTION

It is well known to use disposable wipes for infant care and also for domestic cleaning purposes. Existing wipes are typically pre-moistened sheets of material, made, for example, from viscose, polypropylene or cotton fibres. The sheet of material is usually moistened with an aqueous composition which may contain ingredients such as an anti-bacterial agent, oil or a scent, depending on the intended use for the wipe. The known wipes can be stored and used without the sheet material breaking down. However, the stability of the wipe makes it difficult for the wipe to be safely disposed of by flushing to the sewer. Known wipes must be disposed of in a bin, which may not be hygienic or convenient for a user. It has been found that, when known wipes are flushed away, they may pass out of the toilet bowl, but remain caught within the pipes of a plumbing system. For example, it is common for known wipes to catch on any rough surface or snag within a sewer pipe and remain there to block further matter passing through the pipe and this can lead to a blockage of the sewer pipe.

Indeed, in recent years, representatives from the Water Industry have become concerned about the disposal of inappropriate items to a sewer. This concern has resulted in the UK Water Industry developing a standard protocol to assess individual products, to better understand if they are appropriate for disposal to sewer and whether disposal in this way is sustainable. The protocol includes a disintegration test, used to establish if items disposed of to the sewer network will break down in the drainage, so as not to contribute to blockages.

The disintegration test includes a laboratory based procedure designed to replicate conditions in drains and involves a sample of test product being agitated in a flask of water on an orbital shaker at a specified frequency for a specified time. This is followed by rinsing of the sample through a sieve of a specified perforation, to remove material that has separated from the sample, followed by drying and weighing of the sample. For a sample to pass the test, the sample must start to disintegrate into pieces smaller than 12.5 mm in diameter, following 3 hours of agitation in water in a shaking flask test. At least 50% of the product must break up into pieces of no greater than 12.5 mm diameter within three hours. The remaining pieces should also show a degree of break up, into pieces having a maximum length of 25 mm in their largest dimension Disposable wipes are used by ostomy patients to clean the area around their stoma at the time of removing and disposing of an ostomy bag. Developments in ostomy appliances have led to ostomy bags and liners, which can be hygienically flushed to the sewer. Ostomy bag users also require a cleaning wipe that can be flushed away without the risk of causing a blockage to a drain or sewer pipe.

Known wipes include fabrics which are sensitive to ionic strength to assist breakdown of the material, but there still remains a need for a wipe that is strong enough to be stored and used for cleaning, whilst also being suitable for flushing to the sewer.

The present invention sets out to provide a wipe which is strong enough to be stored and used for cleaning, and which can be flushed away and alleviates one or more of the problems discussed above.

SUMMARY OF THE INVENTION

In a first aspect, the invention provides a wipe which comprises fibres selected from at least one of cellulosic material, polyvinyl acetate (PVA) or a combination thereof; together with a binder which is soluble in water at standard ambient temperature and pressure (SATP).

Preferably, the binder is selected from at least one of carboxymethylcellulose (CMC), alginate, non-fibrous PVA or a combination of at least two thereof.

Preferably, the cellulosic material is selected from at least one of cellulose, rayon regenerated cellulose, polylactic acid (PLA) or modified PLA.

Preferably, the fibres selected from at least one of cellulosic material, polyvinyl acetate (PVA) or a combination thereof are formed into fibres and the fibres are assembled (e.g. woven) into a tissue (for example a woven or non-woven fabric) which is bound by the carboxymethylcellulose (CMC), alginate, non-fibrous PVA or a combination of at least two thereof.

Preferably, a wipe according to this aspect of the invention comprises no other materials.

Advantageously, the PVA has thermoplastic properties. This provides the advantage that the wipe can be folded and pressed into shape with heat so that the fold lines are set into the structure of the wipe.

Preferably, a wipe according to the invention comprises fibres of both cellulosic material and PVA.

Preferably, a wipe according to the invention comprises about 0.2% to about 8% PVA by weight, more preferably about 1% to about 7% PVA by weight, even more preferably about 3% to about 6% PVA by weight, most preferably about 5% PVA by weight.

In an embodiment, the PVA comprises insoluble PVA. In an alternative embodiment, the PVA comprises a mixture of insoluble and soluble PVA.

In a first preferred embodiment, a wipe according to the invention comprises about 5% insoluble PVA by weight.

In an alternative preferred embodiment, a wipe according to the invention comprises about 1% soluble PVA by weight and about 4% insoluble PVA by weight.

Preferably, a wipe according to the invention comprises a binder of CMC.

Preferably, a wipe according to the invention comprises about 1% to about 8% CMC by weight, more preferably about 2% to about 7% CMC by weight, even more preferably about 3% to about 6% CMC by weight, most preferably about 4% CMC by weight.

Advantageously, the binder is soluble in water at room conditions. When the binder disolves, the wipe breaks down.

Advantageously, a wipe according to the invention can be optionally inpregnated with one or more solvents. Preferably, the solvents are non-aqueous solvents.

Preferably, the solvent is liquid barrier film (LBF) fluid.

Preferably, the LBF fluid comprises (a) trimethyl siloxysilicate, hexamethyl disiloxane and cyclo methicone; (b) acrylate and demicone co-polymer; or (c) isododecane and hexamethyl siloxane.

Other oily silicone based solutions could be used. For example, a solvent comprising polydimethyl siloxanes could be used according to the invention. Alternatively, a solvent selected from isododecane, isooctane, heptane or isodecane could be used according to the invention.

Preferably, the solvent comprises a mixture of alcohol and water. Preferably, the mixture comprises more alcohol than water by weight. In a preferred embodiment the solvent comprises 70% alcohol by weight of the solvent. Preferably, the solvent comprises 30% water by weight of the solvent.

Preferably, the solvent comprises an emulsion, dispersion, colloidal suspension. Preferably, the solvent comprises a water phase dispersed in an oily phase. Preferably, water phase carries a cleansing agent in solution, emulsion, dispersion or suspension. Preferably, the cleansing agent is selected from one or more of a soap, surfactant, and detergent.

Preferably, the non-aqueous solvent comprises an alcohol. Preferably, the alcohol is ethanol, isopropyl ethanol or a combination thereof. This provides the advantage of maintaining stability of the wipe until the wipe comes into contact with water.

Preferably, the non-aqueous solvent comprises about 70% alcohol.

Preferably, the solvent comprises an antibacterial agent. Preferably, the antibacterial agent is selected from one or more of chlorhexide gluconate, benzalkonium chloride (BZK), a salt of silver.

In an embodiment, additional solvents could be used. For example, if the wipe is intended for cosmetic use the wipe is preferably impregnated with one or more surfactants. Preferably, the surfactant is selected form an anionic, cationic, zwitterionic, or non-ionic surfactant or combination of at least two or more thereof. Preferably, the zwitterionic surfactant is selected from one or more of sodium laurimino diproprionate. Preferably, the non-ionic surfactant is selected from one or more of amine oxide, ester based sulphate, cocamidopropylamine oxide, polysorbate esters, cetyl or stearyl alcohols.

A wipe according to the invention can be sealed in a sachet and advantageously these solvent(s) do not cause the wipe to break down.

Consequently, the invention provides a package comprising a sachet inside of which is sealed a wipe according to the invention. Preferably, the sachet contains a single wipe and about 1 ml to about 2 ml of non-aqueous solvent.

Preferably, wipes of the invention are included in a multipack having a plurality of wipes. For example, a multipack contains about 5, about 10, about 20, about 30 or about 40 wipes according to the invention.

Preferably the multipack comprises a flow-wrap of wipes according to the invention. Preferably, wipes according to the invention are enclosed in a package and removal of a first wipe at least partially exposes a second wipe so that the second wipe can be easily removed from the package.

Alternatively, the wipes are arranged on a reel. Preferably, the reel is enclosed in a tub.

Alternatively, the wipes are arranged on a roll. Preferably, the wipes are separated by perforations.

A wipe of the invention can be used for surface cleaning or disinfection.

BRIEF DESCRIPTION OF THE DRAWINGS

The invention will now be described by way of example with reference to the accompanying drawings, in which:

FIG. 1 shows the results of a drain line disintegration test on a first wipe according to the invention;

FIG. 2 shows the results of a drain line disintegration test on a first wipe according to the invention impregnated with LBF fluid;

FIG. 3 shows the results of a drain line disintegration test on a second wipe according to the invention;

FIG. 4 shows the results of a drain line disintegration test on a second wipe according to the invention impregnated with a silicone based solvent;

FIG. 5 shows the results of a sewer disintegration test on a first wipe according to the invention;

FIG. 6 shows the results of a sewer disintegration test on a first wipe according to the invention impregnated with LBF fluid;

FIG. 7 shows the results of a sewer disintegration test on a second wipe according to the invention; and FIG. 8 shows the results of a sewer disintegration test on a second wipe according to the invention impregnated with a silicone based solvent.

DETAILED DESCRIPTION OF THE INVENTION

Within the context of this specification the word "comprises" is taken to mean "includes, among other things". It is not intended to be construed as "consists of only".

The word "about" is taken to mean optionally plus or minus 20%, more preferably optionally plus or minus 10%, even more preferably optionally plus or minus 5%, even more preferably optionally plus or minus 2.5%, most preferably optionally plus or minus 1%.

Within the context of this specification, standard ambient temperature and pressure (SATP) is defined as a temperature of 298.15 K (25° C., 77° F.) and an absolute pressure of 100 kPa (14.504 psi, 0.987 atm).

Within the context of this specification, soluble PVA is taken to mean that the PVA dissolves in liquid water at room temperature (about 20° C.) and room pressure (about 101.325 kPa).

Within the context of this specification, the term "non-aqueous solvent" is intended to mean a predominantly hydrophobic solvent. This means that water can be present within the solvent as long as the water molecules are trapped in the solvent and are not free to break down the wipe of the invention. For example, a water in oil emulsion, silicone based solution, or a composition comprising water and alcohol wherein the composition does not comprise predominantly water are "non-aqueous solvents" within the context of the invention. In one example, non-aqueous solvent comprises liquid barrier film (LBF) or silicone fluid. For example, the silicone fluid is a silloxane compound or combination of silloxane compounds. For example, the silicone fluid is selected from one or more of hexamethyl disiloxane, octamethyl trisiloxane, decamethyl tetrasiloxane, decamethyl cyclo pentasiloxane or a combination of at least two or more thereof.

For the purposes of clarity and a concise description, features are described herein as part of the same or separate embodiments; however it will be appreciated that the scope of the invention may include embodiments having combinations of all or some of the features described.

A wipe constructed in accordance with the present invention is approximately about 100 mm by about 150 mm, with a thickness of about 0.5 to about 2 mm. The wipe comprises cellulosic fibres, such as cellulose and/or rayon, which are cross-linked with polyvinylalcohol (PVA) fibres. The PVA material is inert and bio-degradable and acts to bind the cellulosic fibres together, acting almost as a "staple" to maintain the stability and strength of the wipe. The PVA preferably comprises water-soluble PVA and dissolves in contact with water causing the wipe to disintegrate.

The process of manufacture of a wipe according to the invention comprises a producing a slurry of cellulosic material and PVA. The slurry comprises disbursed cellulosic material and PVA fibres. The fibres are deposited onto a screen which comprises a belt. The fibres are drawn by the belt through a drying oven and CMC is sprayed onto the drying fibres. The CMC acts as a binder to bind the fibres together. Dried tissue is extracted from the drying oven and cut into wipes. Preferably, the wipes are impregnated with one or more non-aqueous solvents and each wipe is sealed inside a sachet.

In an alternative embodiment, the process includes spunlace bonding, also known as spunlaced bonding or hydroentangling. In this method, a web of fibres is bonded by interlocking and entangling the fibers about each other with high velocity streams, jets or curtains of water. The web or fabric may have other bonding methods in addition to spunlacing. This method is used in the production of paper by using non-woven manufacturing technology.

The wipe optionally carries a non-aqueous solvent, depending on the wipe's intended use. For example, if the wipe is to be used to apply skin protection, the wipe carries a LBF or silicone fluid, for example a solvent comprising poly dimethyl siloxanes. If a user wishes to apply a silicone coating to their skin, the wipe is passed over the skin and silicone is transferred to act as a skin barrier. If the wipe is to be used to dissolve adhesive material on the skin surface, the wipe preferably carries a citrus oil, such as orange oil. If a user wishes to remove adhesive from the skin's surface, the wipe is passed over the skin and the citrus oil is transferred to remove the adhesive. It is also envisaged that in further embodiments of the invention, the wipe carries an oil-based make-up remover for cosmetic purposes, or a cleaning composition, or an anti-bacterial agent for domestic cleaning purposes or for skin disinfection or cleansing.

In use, the wipe is folded and stored in a sachet. It remains stable in the packaging, which can easily be torn open to remove the wipe for use. In the envisaged medical application of the wipe, it is passed over the skin to apply the non-aqueous fluid contained thereon. After use of the wipe, the wipe is disposed of by placing in a toilet bowl and flushing away to a sewer. The PVA and CMC in the wipe rapidly dissolves with the result that the cross-links between adjacent cellulose fibres are destroyed and the wipe disintegrates before being flushed away. The wipe is fully bio-degradable and will not clog up a plumbing system, drain or sewer.

EXAMPLES

Testing was conducted to establish the preferred composition of the flushable wipe and the method and results are set out below:

Six dry samples of a small medical wipe having a composition A (Fabric A) and four dry samples of a small medical wipe having a composition B (Fabric B) were supplied for testing. (Composition A comprises a wipe according to the invention comprising rayon, 4% insoluble PVA by weight, 1% soluble PVA by weight, and 4% carboxymethyl cellulose binder by weight. Composition B comprises a wipe according to the invention comprising rayon, 5% insoluble PVA by weight and 4% carboxymethyl cellulose binder by weight). Three of the samples having composition A were impregnated with LBF fluid and two of the samples having composition B were impregnated with a silicone based liquid barrier film and they were also submitted for testing. The reason for testing dry and impregnated samples was to separately investigate the properties of the wipe (by testing the dry samples) and any effect the LBF or silicone based liquid barrier film had on the disintegration properties (by testing the impregnated samples).

The UKWIR Flushability Protocol has been developed to assess the suitability for disposal to sewer of potentially flushable products. It comprises of ten stages, at each stage a test(s) is (are) undertaken to assess a particular aspect of the product.

A full product approval requires all stages to be assessed. However, an indication of a products flushability can be gained by undertaking established drainline and sewer disintegration tests. These tests are designed to assess a products ability to break down in the drainage system after being flushed. Experience has shown that it is these disintegration tests, which are undertaken by agitating the product in a shake flask for 3 hours and 6 hours duration respectively, that are likely to be most difficult tests to pass. Hence it will be these tests that mostly define if a product is flushable or not.

With the above in mind, a series of drainline and sewer disintegration tests have been undertaken for each of the fabrics, both in the dry and solvent impregnated states.

Drainline Disintegration Test

The drainline disintegration test consists of a shake flask disintegration test.

A sample (consisting of one medical wipe) was added to one litre of water in a flask, which was agitated for 3 hours at 100 rpm. The extent of product separation after rinsing was measured at the end of the test.

For the product to pass this test at least 50% of the product mass must pass through a 12.5 mm perforated plate sieve and the largest sample of the remaining product must measure no more than 25 mm in its largest dimension.

Six tests were undertaken with Fabric A (three dry and three treated with solvent) and four tests were carried out with Fabric B (two dry and two treated with solvent).

Test Results—Fabric A

The results of the six tests are given in Table 1. This shows the initial mass of the product before testing, the mass retained on the sieve after testing and hence the proportions held on/passing through the sieve.

TABLE 1

Drainline disintegration test results - Fabric A

| Sample ID | DRY A 3 hr - A | DRY A 3 hr - B | DRY A 3 hr - C | A + 2 ml 3 hr - D | A + 2 ml 3 hr - E | A + 2 ml 3 hr - F |
|---|---|---|---|---|---|---|
| Initial dry mass* (g) (Estimated as average of 3 samples.) | | 0.36 | | | 0.48 | |
| Dry mass retained on the 12.5 mm sieve after 3 hours agitation at 100 rpm (g) | 0.29 | 0.30 | 0.28 | 0.27 | 0.30 | 0.28 |

TABLE 1-continued

Drainline disintegration test results - Fabric A

| Sample ID | DRY A 3 hr - A | DRY A 3 hr - B | DRY A 3 hr - C | A + 2 ml 3 hr - D | A + 2 ml 3 hr - E | A + 2 ml 3 hr - F |
|---|---|---|---|---|---|---|
| Percentage passing through the 12.5 mm perforated plate sieve | 19% | 16% | 22% | 44% | 37% | 42% |
| Observations | | See FIG. 1. | | | See FIG. 2. | |
| Pass/fail results | FAIL | FAIL | FAIL | FAIL | FAIL | FAIL |

FIGS. 1 and 2 show photographs of the dry and treated samples respectively, at the following stages during the testing process:
- The sample still in the flask after completing the 3 hours of agitation.
- The sample on the 12.5 mm perforated plate sieve before rinsing.
- The perforated plate sieve after sample rinsing.

The results show that signs of disintegration can be observed at the end of the agitation but the product is still identifiable as a wipe and still mostly in one piece when placed on the sieve. The rinsing of the samples achieves some disintegration of the product.

Test Results—Fabric B

The results of the four tests are given in Table 2. This shows the initial mass of the product before testing, the mass retained on the sieve after testing and hence the proportions held on/passing through the sieve.

TABLE 2

Drainline disintegration test results - Fabric B

| | Sample ID | | | |
|---|---|---|---|---|
| | DRY B 3 hr - G | DRY B 3 hr - H | B + 2 ml 3 hr - I | B + 2 ml 3 hr - J |
| Initial dry mass* (g) (Estimated as average of 2 samples.) | 0.39 | | 0.50 | |
| Dry mass retained on the 12.5 mm sieve after 3 hours agitation at 100 rpm (g) | 0 | 0 | 0 | 0 |
| Percentage passing through the 12.5 mm perforated plate sieve | 100 | 100 | 100 | 100 |
| Observations | See FIG. 3. | | See FIG. 4. | |
| Pass/fail results | PASS | PASS | PASS | PASS |

FIGS. 3 and 4 show photographs of the dry and treated samples respectively, at the following stages during the testing process:
- The sample still in the flask after completing the 3 hours of agitation.
- The sample on the 12.5 mm perforated plate sieve before rinsing.
- The perforated plate sieve after sample rinsing.

The results show a high degree of disintegration of the samples in the flasks, to a degree where single fibres can be identified. Where lumps of fibres were observed in the flasks at the end of the agitation, the gentle rinsing process was sufficient to wash out the fibres so that none were retained on the sieve.

Sewer Disintegration Test

The sewer disintegration test forms part of the UKWIR Flushability Protocol and consists of a shake flask disintegration test. The sample (consisting of one medical wipe) is added to one litre of water in a flask, which is agitated for 6 hours at 150 rpm. The extent of product separation after rinsing is measured at the end of the test.

For the product to pass this test at least 80% of the product mass must pass through a 5.6 mm perforated plate sieve.

Six tests were undertaken with Fabric A (three dry and three treated with LBF fluid) and four tests were carried out with Fabric B (two dry and two treated with silicone based solvent).

Test Results—Fabric A

The results of the six tests are given in Table 3. This shows the initial mass of the product before testing, the mass retained on the sieve after testing and hence the proportions held on/passing through the sieve.

The test requires assessing the disintegration using a perforated plate sieve of 5.6 mm.

Additional analysis of the sample was carried out using a 3.15 mm sieve to demonstrate whether further disintegration of the fabric is observed. Those results are presented here for information.

FIGS. 5 and 6 show photographs of the dry and treated samples respectively, at the following stages during the testing process:
- The sample still in the flask after completing the 6 hours of agitation.
- The sample on the 5.6 mm perforated plate sieve before rinsing.
- The perforated plate sieve after sample rinsing.

The results show a high degree of disintegration of the samples in the flasks: lumps of fibres that make the fabric can be observed in the flasks; these lumps are washed during rinsing and demonstrate that little pressure is required to break-up the product further.

However, a residue was observed on the flasks at the end of the test of the sample with the LBF fluid.

TABLE 3

Sewer disintegration test results - Fabric A

| Sample ID | DRY A 6 hr - A2 | DRY A 6 hr - B2 | DRY A 6 hr - C2 | A + 2 ml 6 hr - D2 | A + 2 ml 6 hr - E2 | A + 2 ml 6 hr - F2 |
|---|---|---|---|---|---|---|
| Initial dry mass* (g) (Estimated as average of 3 samples) | 0.36 | | | 0.48 | | |

TABLE 3-continued

Sewer disintegration test results - Fabric A

| Sample ID | DRY A 6 hr - A2 | DRY A 6 hr - B2 | DRY A 6 hr - C2 | A + 2 ml 6 hr - D2 | A + 2 ml 6 hr - E2 | A + 2 ml 6 hr - F2 |
|---|---|---|---|---|---|---|
| Dry mass retained on the 5.6 mm sieve after 6 hours agitation at 150 rpm (g) | 0 | <0.05 | 0 | 0 | 0 | <0.05 |
| Percentage passing through the 5.6 mm perforated plate sieve | 100% | 94% | 100% | 100% | 100% | 97% |
| Pass/fail results | PASS | PASS | PASS | PASS | PASS | PASS |
| Dry mass retained on the 3.15 mm sieve after 6 hours agitation at 150 rpm (g) | <0.05 g | <0.05 g | 0 | <0.05 g | <0.05 g | <0.05 g |
| Percentage passing through the 3.15 mm perforated plate sieve | 98% | 90% | 100% | 99% | 99% | 89% |
| Observations at 30 min | Still mostly together as one whole wipe, break up has started. | | | Still mostly together as one whole wipe, break up has started. | | |
| At 90 min | Much more broken up but still some clumps. | | | Much more broken up but still some clumps. Water cloudy | | |
| At 3 hours | Mostly broken up, some fibres still together. | | | Mostly broken up, some fibres still together. Water cloudy. | | |
| At 6 hours | Mostly disintegrated, some fibres still together. See FIG. 5. | | | Mostly disintegrated, some fibres still together. Water cloudy and residue evident around the waterline. See FIG. 6. | | |

Test Results—Fabric B

The results of the four tests are given in Table 4. This shows the initial mass of the product before testing, the mass retained on the sieve after testing and hence the proportions held on/passing through the sieve.

The test requires assessing the disintegration using a perforated plate sieve of 5.6 mm.

Additional analysis of the sample was carried out using a 3.15 mm sieve to demonstrate whether further disintegration of the fabric is observed. Those results are presented here for information.

FIGS. 7 and 8 show photographs of the dry and treated samples respectively, at the following stages during the testing process:

The sample still in the flask after completing the 6 hours of agitation.

The sample on the 5.6 mm perforated plate sieve before rinsing.

The perforated plate sieve after sample rinsing.

The results show a high degree of disintegration for both the dry and samples treated with silicone based solvent after the 6 hour test. Even prior to rinsing, very little proportion of the fibres is retained on the sieves.

However, a residue was observed on the flasks at the end of the test of the sample with the silicone fluid.

TABLE 4

Sewer disintegration test results - Fabric B

| | Sample ID | | | |
|---|---|---|---|---|
| | DRY B 6 hr - G2 | DRY B 6 hr - H2 | B + 2 ml 6 hr - I2 | B + 2 ml 6 hr - J2 |
| Initial dry mass* (g) (Estimated as average of 2 samples.) | 0.39 | | 0.50 | |
| Dry mass retained on the 5.6 mm sieve after 6 hours agitation at 150 rpm (g) | 0 | 0 | 0 | 0 |
| Percentage passing through the 5.6 mm perforated plate sieve | 100% | 100% | 100% | 100% |
| Pass/fail results | PASS | PASS | PASS | PASS |
| Dry mass retained on the 3.15 mm sieve after 6 hours agitation at 150 rpm (g) | 0 | 0 | 0 | 0 |
| Percentage passing through the 3.15 mm perforated plate sieve | 100% | 100% | 100% | 100% |
| Observations | After 30 min: already disintegrated, water cloudy. After 90 min/3 hour/ 6 hour: as 30 min. | | After 30 min: already disintegrated, water cloudy. 90 min/3 hour: as 30 min. 6 hour: as 30 min & | |

TABLE 4-continued

Sewer disintegration test results - Fabric B

| Sample ID | | | |
|---|---|---|---|
| DRY B 6 hr - G2 | DRY B 6 hr - H2 | B + 2 ml 6 hr - I2 | B + 2 ml 6 hr - J2 |
| See FIG. 7. | | residue evident around the waterline. See FIG. 8. | |

Summary of Results

In the drainline disintegration test, when less and shorter agitation is applied, Fabric A performs less well than Fabric B. Nevertheless, the level of disintegration observed for fabric A treated with LBF fluid is very promising and disintegration level is close to the pass criteria. Fabric B performs well in the drainline disintegration test.

Both A and B types of fabric show very good performance when assessed against the sewer disintegration test, with most or all of the products disintegrating into small fibres.

The results are summarised in Table 5 below:

TABLE 5

Summary of results

| | | Sample ID | | | |
|---|---|---|---|---|---|
| | | DRY A | A + 2 ml | DRY B | B + 2 ml |
| Drainline disintegration | Pass criteria | At least 50% of the product mass shall pass through a 12.5 mm perforated plate sieve and the largest sample of the remaining product shall measure no more than 25 mm in their larger dimension. | | | |
| | Percentage passing through the 12.5 mm sieve after 3 hours agitation at 100 rpm (+observation on remaining material on sieve) | 16 to 22% (pieces above 25 mm on sieve) | 37% to 44% (pieces above 25 mm on sieve) | 100% (n/a) | 100% (n/a) |
| | Conclusion | FAIL | FAIL | PASS | PASS |
| Sewer disintegration test | Pass criteria | At least 80% of the product mass shall pass through a 5.6 mm perforated plate sieve. | | | |
| | Percentage passing through the 5.6 mm sieve after 6 hours agitation at 150 rpm | 94% to 100% | 97% to 100% | 100% | 100% |
| | Conclusion | PASS | PASS | PASS | PASS |

The above described embodiments have been given by way of example only, and the skilled reader will naturally appreciate that many variations could be made thereto without departing from the scope of the claims.

What is claimed is:

1. A wipe which comprises fibres of
   (a) polylactic acid (PLA), modified PLA, or cellulosic material and
   (b) polyvinyl acetate (PVA); together with a binder which is soluble in water at standard ambient temperature and pressure (SATP), wherein the binder is carboxymethylcellulose (CMC); and wherein the wipe comprises about 5% PVA fibres by weight and about 4% CMC by weight, and is water soluble at standard ambient temperature, or passes drainline and sewer disintegration tests as defined in the UKWIR flushability protocol, wherein said protocol comprises a dispersibility shake flask test having a rinse time of about 1 minute and a sieve size of about 5.6 mm, and wherein the PVA fibres comprise a mixture of about 4% PVA fibres which are insoluble in liquid water at 20° C. and 101,325 kPA and about 1% PVA fibres which are soluble in liquid water at 20° C. and 101,325 kPA.

2. A wipe according to claim 1, wherein the cellulosic material is selected from at least one of cellulose, rayon, regenerated cellulose, or a combination of at least two or more thereof.

3. A wipe according to claim 1, wherein the fibres are formed into fibres and the fibres are assembled into a tissue which is bound by the binder.

4. A wipe according to claim 1, which comprises no other materials.

5. A wipe according to claim 1, wherein the wipe is impregnated with one or more non-aqueous solvents.

6. A wipe according to claim 5, wherein the non-aqueous solvents are selected from one or more of liquid barrier film (LBF) fluid, oily silicone based solutions, polydimethyl siloxanes, or one or more surfactants.

7. A wipe according to claim 5, which carries a non-aqueous solvent, selected from a LBF or silicone fluid, a citrus oil optionally selected from orange oil, an oil-based make-up remover for cosmetic purposes, or a cleaning composition comprising a surfactant, or an anti-bacterial agent.

8. A sachet inside which is sealed a wipe according to claim 1.

9. A sachet according to claim 8, wherein the sachet further contains about 1 ml to about 2 ml of non-aqueous solvent.

10. A wipe according to claim 7, wherein the surfactant is a non-ionic surfactant.

11. A wipe according to claim 10, wherein the non-ionic surfactant is an amine oxide based non-ionic surfactant.

* * * * *